(12) United States Patent
Saito

(10) Patent No.: US 8,506,082 B2
(45) Date of Patent: Aug. 13, 2013

(54) OPHTHALMIC APPARATUS, ADAPTIVE OPTICAL SYSTEM, AND IMAGE GENERATING APPARATUS

(75) Inventor: Kenichi Saito, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 203 days.

(21) Appl. No.: 13/090,548

(22) Filed: Apr. 20, 2011

(65) Prior Publication Data

US 2011/0279778 A1  Nov. 17, 2011

(30) Foreign Application Priority Data

May 17, 2010 (JP) ................................. 2010-113423

(51) Int. Cl.
 *A61B 3/10* (2006.01)
(52) U.S. Cl.
 USPC .......................................................... 351/221
(58) Field of Classification Search
 USPC ......................................... 351/221, 205, 246
 See application file for complete search history.

(56) References Cited

U.S. PATENT DOCUMENTS

| 7,394,595 B2 * | 7/2008 | Somani et al. ................ 359/619 |
| 7,896,498 B2 * | 3/2011 | Munger et al. ................ 351/221 |
| 2011/0001930 A1 | 1/2011 | Levecq | |

FOREIGN PATENT DOCUMENTS

| JP | 4157839 B2 | 7/2008 |
| WO | 03/020121 A1 | 3/2003 |
| WO | 2008/050285 A2 | 5/2008 |
| WO | 2008/113937 A2 | 9/2008 |

OTHER PUBLICATIONS

U.S. Appl. No. 13/069,806, filed Mar. 23, 2011, Inventor Saito et al.*
U.S. Appl. No. 13/132,101, filed Jun. 1, 2011, Inventor Yuasa et al.*
Austin Roorda, Adaptive optics scanning laser ophthalmoscopy, Optics Express, vol. 10, No. 9, pp. 405-412, May 6, 2002.

* cited by examiner

*Primary Examiner* — Hung Dang
(74) *Attorney, Agent, or Firm* — Fitzpatrick, Cella, Harper & Scinto

(57) ABSTRACT

An ophthalmic apparatus includes an aberration correction unit which corrects aberration occurring in light irradiating an eye to be examined; and a common optical system which is commonly provided for an optical path of irradiated light on the aberration correction unit and an optical path of reflected light from the aberration correction unit. The common optical system includes at least one optical element, and areas through which the irradiated light and the reflected light respectively pass overlap each other on the optical element.

30 Claims, 7 Drawing Sheets

OPHTHALMIC APPARATUS, ADAPTIVE OPTICAL SYSTEM, AND IMAGE GENERATING APPARATUS

BACKGROUND OF THE INVENTION

1. Field of the Invention

The present invention relates to an ophthalmic apparatus, an adaptive optical system, and an image generating apparatus using the adaptive optical system and, more particularly, to an adaptive optical system which corrects wavefront aberration occurring at an object to be detected and an image generating apparatus including the adaptive optical system.

2. Description of the Related Art

Recently, a technique of adaptive optics (adaptive optical technique) which corrects low- to high-order wavefront aberrations by an adaptive optical system using an optical element capable of actively correcting optical characteristics has been put into practice and applied to various fields. This technique corrects high-order wavefront aberration by a wavefront aberration correction device such as a deformable mirror or a spatial optical modulator by sequentially measuring the wavefront aberration of probe light or signal light with a wavefront sensor, which occurs due to variations in the characteristics of an object to be measured itself, measurement environment, or the like. The above optical element was used at first to improve resolution by correcting wavefront disturbance due to atmospheric fluctuations at the time of astronomical observation. As a field in which the effect of the introduction of this optical element is large, in addition to the field of astronomical observation, the field of eye retina examination systems has attracted attention.

As an ophthalmic apparatus, an SLO (Scanning Laser Ophtalmoscope) which acquires a two-dimensional image of the retina as a plane is known as well as a fundus camera. In addition to a fundus camera and SLO, an OCT (Optical Coherence Tomography) is known, which noninvasively acquires a tomogram of the retina. Fundus cameras, SLOs, and OCTs have already been on the market for years.

An SLO and OCT are designed to acquire two-dimensional or three-dimensional images of the retina by two-dimensionally scanning a light beam on the retina using a deflector and simultaneously measuring reflected/backscattering light. The spatial resolution (to be referred to as "transverse resolution" hereinafter) of an acquired image in the in-plane direction (transverse direction) of the retina is basically determined by the diameter of a beam spot scanned on the retina. It is possible to reduce the diameter of a beam spot condensed on the retina by increasing the diameter of a beam striking the eye. The uniformity of the curved surface shapes and refractive indices of the cornea and crystalline lens, which mainly have a function of refracting light, is imperfect. Such imperfection causes high-order aberration on the wavefront of transmitted light. Even if, therefore, a thick beam is made to strike the eye, a spot on the retina cannot be condensed to a desired diameter but rather spreads. As a result, the transverse resolution of an obtained image decreases, and the S/N of an acquired image signal also decreases in a confocal optical system. Conventionally, therefore, it has been a general practice to cause a thin beam having a diameter of about 1 mm, which is robust against the influence of the aberration of the eye optics, to strike the eye to form a spot having a diameter of about 20 µm on the retina.

On the other hand, it is reported that even when a thick beam having a diameter of about 7 mm is made to strike the eyeball by using an adaptive optical technique, it is possible to condense the beam to about 3 µm, which is close to the diffraction limit on the retina, by wavefront correction, thereby acquiring a high-resolution SLO or OCT image.

An adaptive optical system basically has an arrangement like that shown in FIG. 4. This arrangement exemplifies the confocal optical system of an SLO, which includes an adaptive optical system constituted by a collimator lens 30 and concave mirrors 31a, 32, 33, and 34 and an ocular optical system constituted by concave mirrors 35 and 36. The adaptive optical system and the ocular optical system guide a beam emitted from an illumination light source (not shown) and irradiated through an end portion of an optical fiber 9 to an eyeball 6. The anterior ocular segment such as the cornea condenses this beam on a retina 61. The reflected/backscattering light from the retina 61 propagates through the reverse optical path and is coupled to the optical fiber 9 again. The beam is then branched by a fiber coupler (not shown) and guided to a photodetector. The photodetector detects the intensity of the beam. Further scanning this beam on the retina 61 using two-dimensional scanner mirrors 51 and 52 will obtain a two-dimensional retina image.

In this case, the adaptive optical system includes a wavefront correction device 1 and a wavefront sensor 2. Both the wavefront correction device 1 and the wavefront sensor 2 are arranged in an optically conjugate relationship with the position of the anterior ocular segment (an eyeball pupil 62 to be precise) of the eyeball 6. This makes it possible to detect wavefront aberration caused by the eyeball optics in a qualitatively and quantitatively equivalent state and correct the aberration.

The reflected/backscattering light from the retina 61 has a disturbed wavefront due to the influence of the characteristics of the anterior ocular segment and propagates through the ocular optical system and the adaptive optical system. The beam is then partially reflected by a beam branching member 41 and strikes the wavefront sensor 2. The signal detected by the wavefront sensor 2 is sent to a computer 8 to generate a driving signal which cancels out the calculated wavefront aberration, thereby controlling the wavefront correction device 1. The wavefront correction device 1 corrects the disturbed wavefront in this manner to generate a wavefront with little aberration, which is suitably coupled to the optical fiber 9. The reason why the overall system has the arrangement of an eccentric reflective optical system is that a confocal optical system using a lens prevents reflected light from the lens surface from striking the wavefront sensor 2 simultaneously with return light from the retina.

According to Japanese Patent No. 4157839 which applies an adaptive optical system to an SLO, a concave mirror which forms a parallel beam to be made to strike a deformable mirror is placed adjacent to a concave mirror which receives reflected light from the deformable mirror, thereby minimizing the incident angle of light on the mirror and reducing the aberration of the optical system.

The technique disclosed in A. Roorda et al., "Adaptive optics scanning laser ophthalmoscopy", OPTICS EXPRESS/ Vol. 10, No. 9/2002 also uses the arrangement of an adaptive optical OCT using such an eccentric reflective optical system, which uses a deformable mirror as a wavefront correction device. This arrangement uses two deformable mirrors, one for the correction of low-order aberration requiring a large correction amount and the other for the correction of high-order aberration requiring a small correction amount.

The first problem in the adaptive optical system is that the size of the optical system is large. This is because this optical system needs to be designed to suppress aberration while arranging the wavefront correction device 1 and the wavefront sensor 2 so as to make them optically conjugate to each other. If the residual aberration of the optical system is large, the wavefront correction device 1 must also correct this. When correcting it as well as the aberration of the eye, the wavefront correction device 1 may lack in correction stroke which determines the correction amount of the wavefront correction device 1. In the eccentric reflective optical system shown in FIG. 4, in particular, the larger the incident angle of light on the concave mirrors 32 and 33, the larger the aberration including astigmatism. Since the diameters of the concave mirrors 32 and 33 are determined by the size of the wavefront correction device 1, it is necessary to increase the focal lengths of the concave mirrors 32 and 33 with reductions in incident angle.

Reducing the diameter of the wavefront correction device 1 can reduce the diameter of an incident beam 71 and the focal length of the concave mirror 32. In most cases, however, the above deformable mirror or a spatial optical modulator using a liquid crystal is used as the wavefront correction device 1. Many of these devices have diameters exceeding 10 mm, and only a few of them have diameters smaller than 5 mm. In addition, the correction strokes of such devices are short. The thinner a beam, the smaller the focal length of a concave mirror can be. It is therefore conceivable to use a method of making a beam with a small diameter strike the wavefront correction device 1 with a large diameter. This, however, decreases the number of segments (pixels) effective at the time of correction, resulting in a deterioration in correction performance especially for high-order aberration.

According to Japanese Patent No. 4157839, the incident angle is reduced by eliminating the space between the adjacent concave mirrors. However, since it is impossible to bring the concave mirror closer to each other, it is impossible to further reduce the incident angle. In addition, it is conceivable to use a method of using a lens system as an optical system instead of mirrors by reducing the incident angle of light on the wavefront correction device 1 to zero, that is, making the incident angle and the reflection angle be coaxial. In this case, however, it is necessary to branch incident light from reflected light by using a half mirror or the like. This reduces the efficiency to at least ¼, and hence it is impossible to secure sufficient signal light intensity in a device which examines a sample exhibiting considerably low reflectivity like the retina. It is therefore difficult to use such a method.

Under these circumstances, therefore, an adaptive optical system requires a large area of several tens square cm, and hence it is difficult to implement commercial equipment with a proper size.

SUMMARY OF THE INVENTION

The present invention provides an adaptive optical system with a compact size.

In addition, the present invention provides an adaptive optical system which requires no complicated arrangement and has a compact size while suppressing residual aberration of an optical system even in the use of a wavefront correction device having a large effective area.

According to one aspect of the present invention, there is provided an ophthalmic apparatus comprising: an aberration correction unit adapted to correct aberration occurring in light irradiating an eye to be examined; and a common optical system commonly provided for an optical path of irradiated light on the aberration correction unit and an optical path of reflected light from the aberration correction unit, wherein the common optical system includes at least one optical element, and areas through which the irradiated light and the reflected light respectively pass overlap each other on the optical element.

According to another aspect of the present invention, there is provided an adaptive optical system comprising: a wavefront sensor which receives reflected light of light irradiated from a light source to an object to be detected and detects a wavefront of the object; a wavefront correction unit adapted to, placed at a position optically conjugate to the wavefront sensor, correct wavefront aberration obtained based on a detection result on the wavefront detected by the wavefront sensor; and a common optical system which causes light from a first intermediate image irradiated from the light source and condensed to propagate through a first optical path, causes the propagating light to strike the wavefront correction unit, causes light reflected by the wavefront correction unit to propagate through a second optical path different from the first optical path, and condenses the light as a second intermediate image different from the first intermediate image, wherein the wavefront correction unit is placed at a position of an incident pupil of the common optical system, and the first intermediate and the second intermediate image are condensed on an image plane of the common optical system having the incident pupil.

The present invention can provide an adaptive optical system having a compact size without requiring any complicated arrangement.

In addition, it is possible to provide an adaptive optical system having a compact size without requiring any complicated arrangement while suppressing residual aberration of an optical system even in the use of a reflection type wavefront correction device with a large effective area.

Further features of the present invention will become apparent from the following description of exemplary embodiments with reference to the attached drawings.

DESCRIPTION OF THE EMBODIMENTS

First Embodiment

Figure 1:
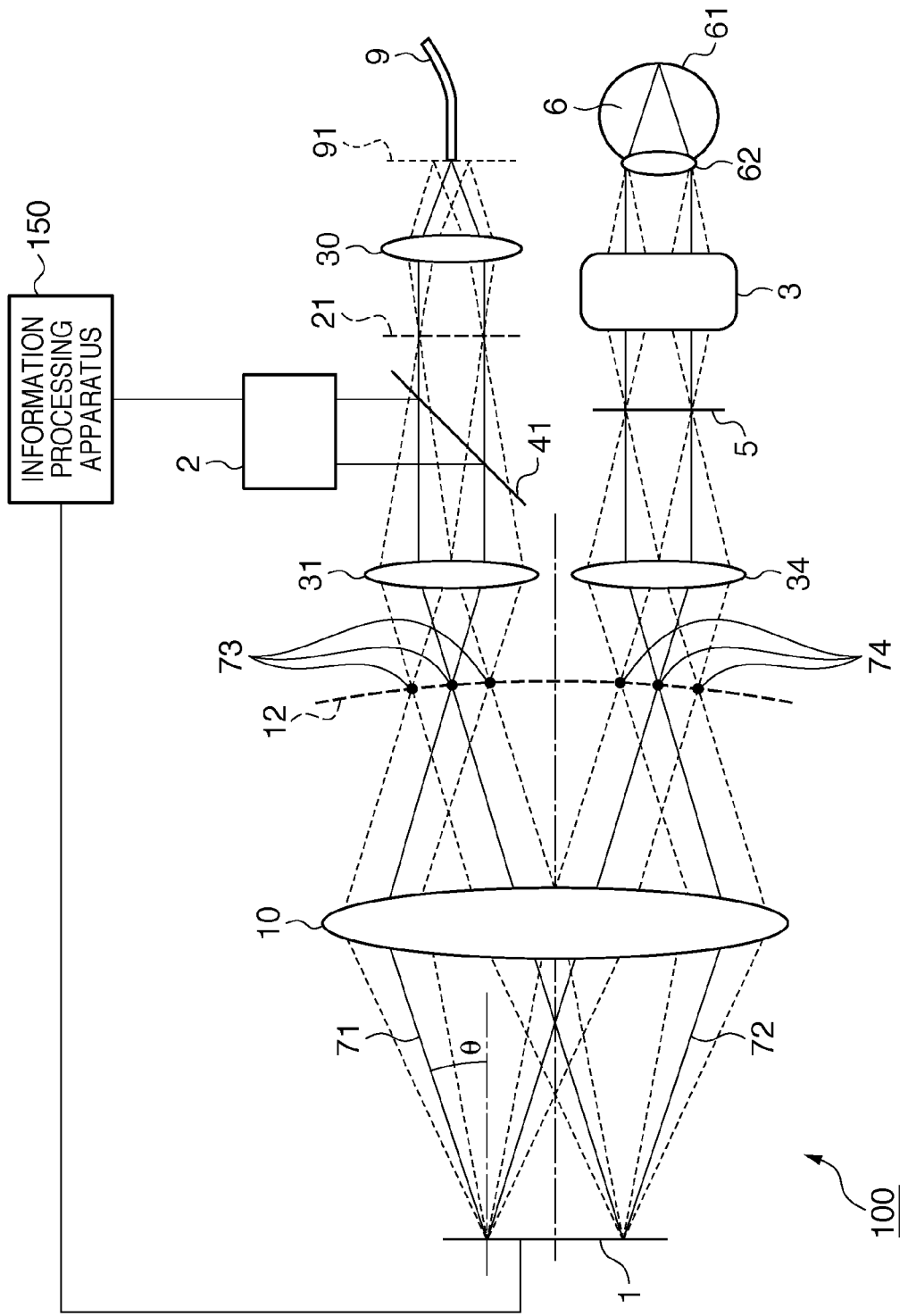
FIG. 1 is a view showing the basic concept of an adaptive optical system according to an embodiment of the present invention.

An adaptive optical system according to an embodiment of the present invention will be described with reference to FIG. 1. Referring to FIG. 1, the solid lines indicate light beams showing the image formation relationship between laser beams irradiated from an optical fiber 9, and the broken lines indicate light beams indicating the image formation relationship between the pupils of the optical systems. An adaptive optical system 100 is a confocal optical system constituted by an adaptive optical system and an ocular optical system, with a plane including an end portion (fiber end) of the optical fiber 9, which irradiates laser beams, being an object plane 91, and a retina 61 of an eyeball 6 being an image plane.

Light from a light source (not shown) which propagates through the optical fiber 9 is irradiated as divergent light from a fiber end and collimated by a collimator lens 30. The collimated light beam is then transmitted through a beam branching member 41 and condensed at the position of a first intermediate image 73 by an optical element 31. A beam spreading from the position of the first intermediate image 73 condensed on the incident side of a common optical system 10 is transmitted through the first optical path of the common optical system 10 and collimated by the common optical system 10. The collimated beam strikes a reflection type wavefront correction device 1 at an incident angle θ relative to the horizontal direction.

Figure 4:
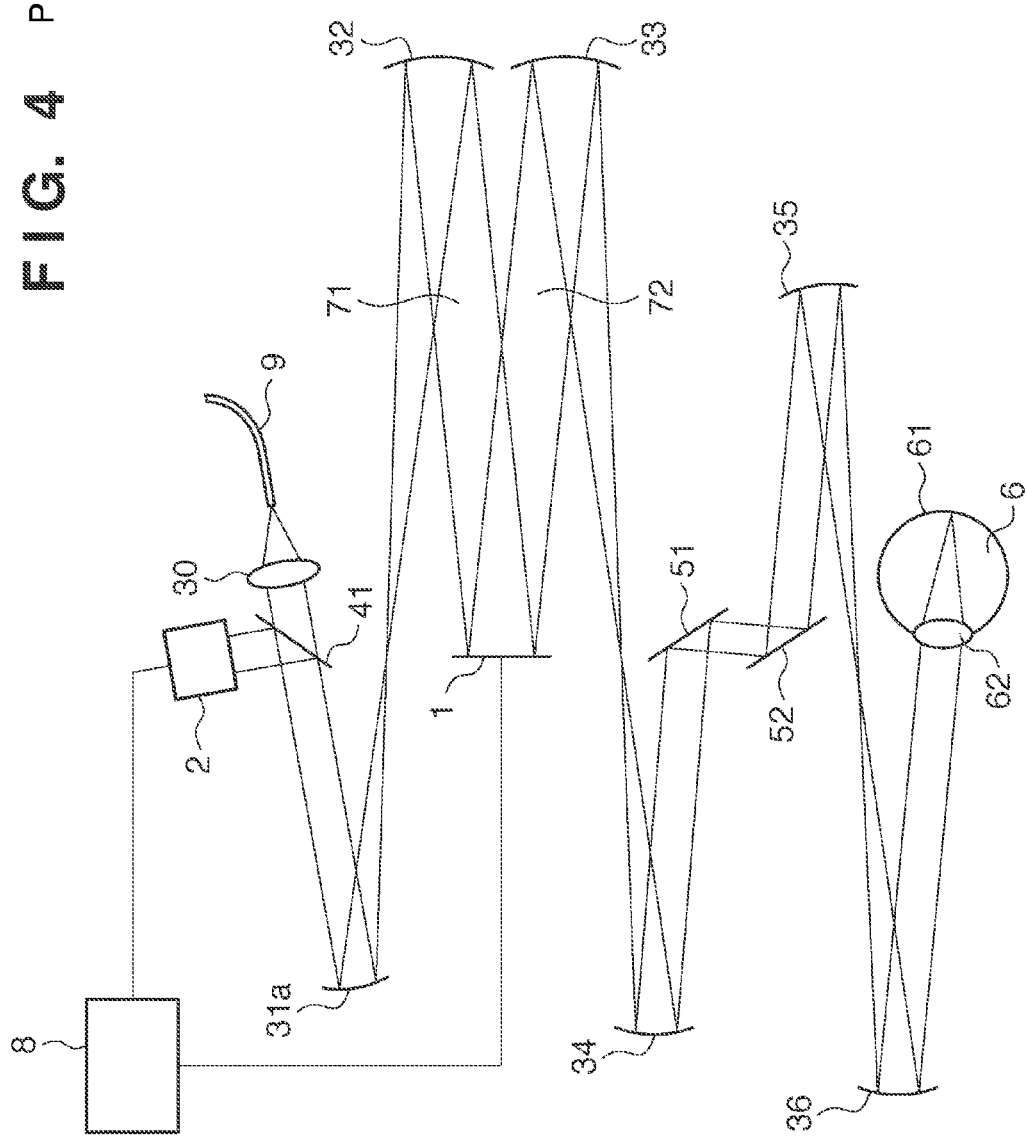
FIG. 4 is a view showing the arrangement of a conventional adaptive optical system.

The wavefront correction device 1 has a reflecting surface which receives the light collimated by the common optical system 10 and reflects the received light to the common optical system 10. The reflecting surface of the wavefront correction device 1 is deformable. The wavefront correction device 1 can correct the wavefront aberration of the object by changing the shape of the reflecting surface so as to cancel out the aberration. The calculation of the driving amount of the wavefront correction device 1 to change the shape of the reflecting surface will be described later. A reflected beam 72 reflected by the reflecting surface of the wavefront correction device 1 is transmitted through the second optical path of the common optical system 10 again and condensed at the position of a second intermediate image 74. Light spreading from the position of the second intermediate image 74 condensed on the exit side (reflection side) of the common optical system 10 is collimated by the optical element 34 and strikes a deflection element 5 to be deflected in a two-dimensional direction. In this case, the concave mirrors 32 and 33 in the prior art shown in FIG. 4 are formed as the common optical system 10. This obviates the need to completely separate an incident beam 71 from the reflected beam 72 on the common optical system 10 in the optical system. From this viewpoint, no limitation is imposed on the incident angle θ. It is therefore possible to reduce the incident angle of light on the wavefront correction device 1 and also to reduce the incident angle of light on the common optical system 10. This can reduce the correction residue of the wavefront correction device 1 and suppress various kinds of aberration such as astigmatism caused by the common optical system 10.

The deflection element 5 deflects a beam in a two-dimensional direction. An ocular optical system 3 then converts the beam into a beam having a predetermined desired diameter, which strikes the eyeball 6 as an object to be examined. The beam is formed into an image on the retina 61 and scanned within a predetermined range on the retina 61. Thereafter, when return light reflected/scattered from the point at which the beam is condensed on the retina 61 passes through an eyeball pupil 62, the return beam is influenced by the aberration of the eyeball to have a disturbed wavefront. This light reversely propagates from the ocular optical system 3 to the optical element 31. The beam branching member 41 located between the optical element 31 and the collimator lens 30 splits the return light nearly collimated by the optical element 31. The beam branching member 41 reflects part of the return light split by the beam branching member 41. This light then strikes a wavefront sensor 2. The remaining part of the light is transmitted through the beam branching member 41. This light then strikes the optical fiber 9 and is coupled to it through the collimator lens 30.

As the wavefront sensor 2, for example, a sensor based on the Shack-Hartmann system is used. The system on which the wavefront sensor 2 is based is not limited to the Shack-Hartmann system, and another system may be used. The wavefront sensor 2 detects the wavefront of the return light as a Hartmann image. The detection result obtained by the wavefront sensor 2 is sent to an information processing apparatus 150. The information processing apparatus 150 calculates wavefront aberration and a driving value for the wavefront correction device 1 to correct the wavefront aberration. The wavefront correction device 1 is driven based on the driving value calculated by the information processing apparatus 150 to correct the wavefront aberration. This can improve the coupling efficiency of return light to the optical fiber 9 to an extent near the efficiency corresponding to the diffraction limit. In this case, it is possible to use, as the wavefront correction device 1, either a deformable mirror capable of changing the shape of the reflecting surface or a spatial optical modulator.

In order to accurately detect and correct wavefront aberration occurring at the anterior ocular segment and simultaneously make the coupling efficiency for the optical fiber 9 high while the wavefront aberration is properly corrected, it is necessary to establish the following optical positional relationship. That is, the wavefront correction device 1 and the wavefront sensor 2 (a micro-lens array surface (an exit pupil 21 of a collimator lens) as the detection surface of the wavefront sensor 2) need to have an optically conjugate positional relationship. In addition, the ocular optical system 3, a chin rest (not shown), and the like are arranged to set both the wavefront correction device 1 and the wavefront sensor 2 in an optically conjugate positional relationship with the position of the anterior ocular segment (the eyeball pupil 62 to be precise) of the eyeball 6. The first intermediate image 73 is an image of light condensed by the optical element 31 having the position of the incident pupil set to the exit pupil 21 of the collimator lens. A requirement for setting a conjugate positional relationship is to make both the position of the first intermediate image 73 and the position of the second intermediate image 74 of the optical element 34 with the position of the incident pupil being set to the deflection element 5 coincide with the position of an image plane 12 of the common optical system 10 with the position of the incident pupil coinciding with the position of the wavefront correction device 1. The wavefront correction device 1 is placed at the position of the incident pupil of the common optical system 10. The first intermediate image 73 and the second intermediate image 74 are condensed on the image plane 12 of the common optical system 10 with reference to the position of the incident pupil.

Although the angles of incident light beams from the respective optical systems (the adaptive optical system and the ocular optical system) to the image plane must coincide with each other, the respective optical systems may be designed to be image-side telecentric. If the common optical system 10 is not image-side telecentric, the collimator lens 30, the optical element 31 (also called the first optical element provided on the optical path of the light irradiating the wavefront correction device 1), and the optical element 34 (also called the second optical element provided on the optical path of the light reflected from the wavefront correction device 1) are made eccentric relative to the common optical system 10 (the optical axes of the first and second optical elements are shifted to the optical axis side of the common optical system). This can reduce the aberration occurring at the common optical system 10.

Figure 2:
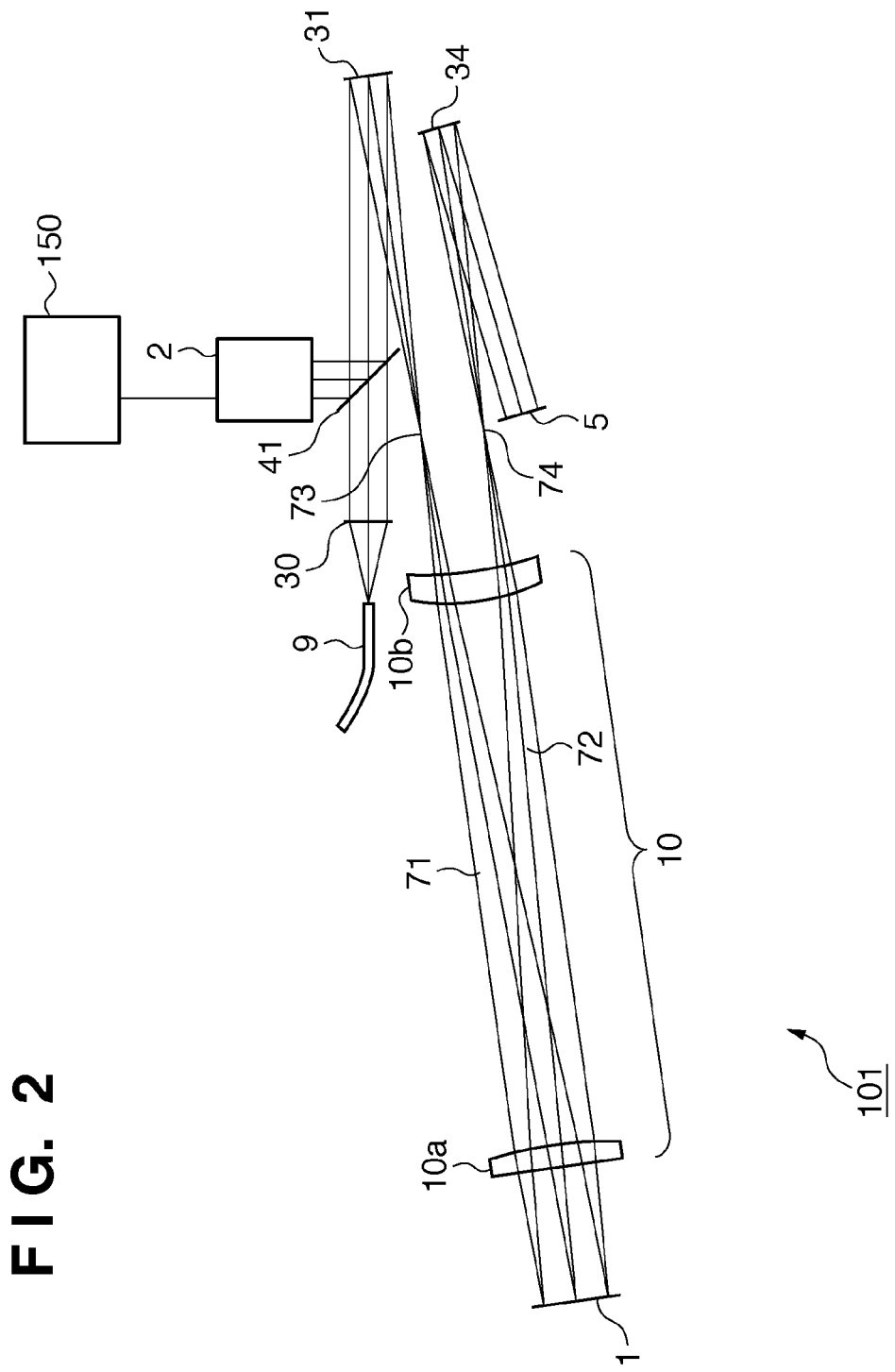
FIG. 2 is a view showing the arrangement of an adaptive optical system according to the first embodiment of the present invention.

The concrete arrangement of the adaptive optical system in FIG. 1 will be described next with reference to FIG. 2. FIG. 2 shows an adaptive optical system 101 extending from a fiber end of the optical fiber 9 to the deflection element 5 (scanner) and the principal ray and marginal rays of a beam, with the portion after the ocular optical system 3 shown in FIG. 1 being omitted. The basic arrangement is the same as that shown in FIG. 1, and the same reference numerals denote the same elements.

Source light having wavelengths of 840 nm and a wavelength width of 50 nm irradiated from a light source (not shown) propagates through the optical fiber 9 (single-mode fiber) and is irradiated as divergent light from an end face of the optical fiber 9. The collimator lens 30 collimates the light irradiated from the optical fiber 9. The optical fiber 9 has a core diameter of 5 µm. The collimator lens 30 has a focal length of 15 mm. Therefore, the parallel beam has a beam diameter of about 3.2 mm with a relative intensity 1/e2. The relationship between a distance dk between the principal ray of an incident beam on the wavefront correction device 1 and the principal ray of a reflected beam from the wavefront correction device 1, and a beam diameter dK of an optical element of the common optical system satisfies dk≦2·Dk.

The optical element 31 (spherical mirror) with a focal length of 60 mm condenses this parallel beam transmitted through the beam branching member 41 (beam splitter) at the position of the first intermediate image 73. The parallel beam which is transmitted through the common optical system 10 constituted by two spherical lenses and collimated strikes the wavefront correction device 1 at an incident angle of about 3° relative to the horizontal direction. The wavefront correction device 1 reflects the incident parallel beam collimated by the common optical system 10 to the common optical system 10. The reflected light is condensed at the position of the second intermediate image 74 again through the common optical system 10. The focal length of the common optical system 10 is 10 mm, and the diameter of an incident beam is about 5.6 mm. In this case, the wavefront correction device 1 is placed at the position of the incident pupil of the common optical system 10, and the positions of two intermediate images (the positions of the first and second intermediate images 73 and 74) are set on the image plane 12 (see FIG. 1) of the common optical system 10. In addition, the incident beam 71 on the wavefront correction device 1 and the reflected beam 72 from the wavefront correction device 1 propagate symmetrically about the optical axis of the common optical system 10. Two lenses 10a and 10b constituting the common optical system 10 are arranged as a confocal optical system having an optical axis coinciding with an axis which passes through the center of the reflecting surface of the wavefront correction device 1 (the reflecting point of the principal ray of incident light) and is perpendicular to the reflecting surface of the wavefront correction device 1. Materials and shapes are set for the two lenses 10a and 10b so as to reduce various kinds of aberrations including chromatic aberration. The two spherical lenses 10a and 10b are combined to further shorten the distances from the wavefront correction device 1 to the position of the first intermediate image 73 and to the position of the second intermediate image 74. To further reduce the aberration of the common optical system 10, the number of lenses may be increased or an aspherical lens may be used. In order to maintain the transmittance of the common optical system 10, it is preferable to minimize the number of lenses. When using an aspherical lens, it is necessary to use an aspherical shape having a single extreme instead of a complicated shape having a plurality of extremes in consideration of the fact that an incident beam and a reflected beam overlap on the lens surface of the common optical system 10.

The light spreading from the position of the second intermediate image 74 is collimated again by the optical element 34 (spherical mirror) having a focal length of 50 mm afterward, and strikes the deflection element 5 (scanner). In this case, a beam has a diameter of about 2.7 mm and is deflected in a two-dimensional direction by the deflection element 5 (scanner). The ocular optical system 3 (FIG. 1), which is not shown in FIG. 2, converts the beam into a beam having a desired diameter. This beam strikes an object to be examined (eyeball) which is not shown in FIG. 2 and formed into an image on the retina 61. This beam is then scanned in a predetermined range on the retina 61. The reflected/backscattering light from a beam irradiation point on the retina 61 propagates as return light through the inverse optical path. Part of the return light reflected by the beam branching member 41 (beam splitter) strikes the wavefront sensor 2.

The return light detected by the wavefront sensor 2 is sent to the information processing apparatus 150. The information processing apparatus 150 detects wavefront aberration from the return light reflected by the beam branching member 41, and calculates a correction amount for dividing the wavefront correction device 1 so as to cancel out the detected wavefront aberration. The wavefront correction device 1 is driven based on the calculated correction amount. Driving the wavefront correction device 1 will properly correct the wavefront of the return light. The light transmitted through the beam branching member 41 (beam splitter) is properly formed into an image on an end face of the optical fiber 9 through the collimator lens 30. A sensor (not shown) detects the intensity of the return light. The detection result is input to the information processing apparatus 150. The information processing apparatus 150 generates a two-dimensional or three-dimensional image based on the detection result obtained by the sensor (not shown) and the intensity of the return light.

Figure 3:
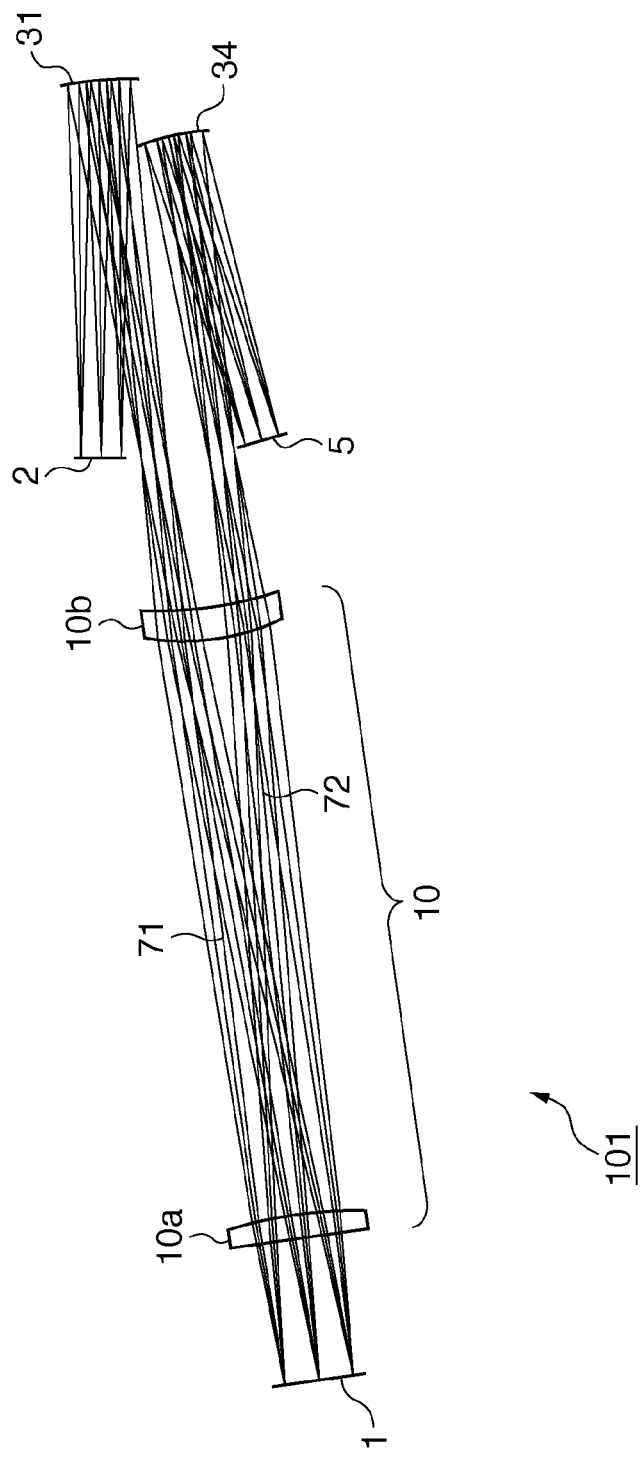
FIG. 3 is a view showing the arrangement of the adaptive optical system according to the first embodiment of the present invention.

A ray diagram showing the image formation relationship between a position corresponding to the wavefront sensor 2 and the three pupil conjugate positions of the wavefront correction device 1, deflection element 5, and deflection element 5 (scanner) will be described with reference to FIG. 3. The deflection element 5 (scanner) is conjugate to the eyeball pupil 62 (FIG. 1) through the ocular optical system 3 (FIG. 1), and the position corresponding to the wavefront sensor 2 and the position of the wavefront correction device 1 are also have a conjugate relationship with the eyeball pupil 62 (FIG. 1). This makes it possible to accurately perform wavefront measurement and wavefront correction.

The following is optical data associated with the adaptive optical system 101. In this case, the origin of the XYZ-coordinate system indicates the center of the exit end face of the optical fiber 9, the Z-axis is the propagating direction of exit light from the optical fiber 9, and X- and Y-axes are directions perpendicular to the Z-axis on the stop surface. In addition, n and ν of the glass material respectively indicate a refractive index and an Abbe number.

| Surface Number (n, ν) | Radius of Curvature | X Position | Y Position | Z position | X-axis rotation | Glass |
|---|---|---|---|---|---|---|
| 1 | ∞ | 0.000 | 0.000 | 0.000 | 0.000 | |
| 2 | ∞ | 0.000 | 0.000 | 0.000 | 0.000 | |
| stop | ∞ | 0.000 | 0.000 | 15.000 | 0.000 | |
| 4 | ∞ | 0.000 | 0.000 | 15.000 | 0.000 | |
| 5 | −120.000 | 0.000 | 0.000 | 75.000 | 4.000 | (reflection) |
| 6 | ∞ | 0.000 | 0.000 | 75.000 | 8.000 | |
| 7 | ∞ | 0.000 | −8.350 | 15.584 | 8.000 | |
| 8 | ∞ | 0.000 | −8.350 | 15.584 | 8.000 | |
| 9 | ∞ | 0.000 | −8.350 | 15.584 | 7.766 | |
| 10 | ∞ | 0.000 | −13.536 | 16.291 | 7.766 | |
| 11 | 94.008 | 0.000 | −16.957 | −8.791 | 7.766 | 1.48749 70.41 |
| 12 | 38.211 | 0.000 | −17.633 | −13.745 | 7.766 | |
| 13 | −118.598 | 0.000 | −30.214 | −105.993 | 7.766 | 1.72889 46.08 |
| 14 | 458.614 | 0.000 | −30.754 | −109.956 | 7.766 | |
| 15 | ∞ | 0.000 | −30.754 | −109.956 | 7.766 | |
| 16 | ∞ | 0.000 | −33.749 | −131.917 | 7.766 | (reflection) |
| 17 | ∞ | 0.000 | −33.749 | −131.917 | 7.766 | |
| 18 | 458.614 | 0.000 | −30.754 | −109.956 | 7.766 | 1.72889 46.08 |
| 19 | −118.598 | 0.000 | −30.214 | −105.993 | 7.766 | |
| 20 | 38.211 | 0.000 | −17.633 | −13.745 | 7.766 | 1.48749 70.41 |
| 21 | 94.008 | 0.000 | −16.957 | −8.791 | 7.766 | |
| 22 | ∞ | 0.000 | −13.541 | 16.256 | 7.766 | |
| 23 | ∞ | 0.000 | −18.727 | 16.963 | 7.766 | |
| 24 | ∞ | 0.000 | −18.727 | 16.963 | 7.766 | |
| 25 | −100.000 | 0.000 | −11.971 | 66.504 | 11.766 | (reflection) |
| 26 | ∞ | 0.000 | −11.971 | 66.504 | 15.766 | |
| 27 | ∞ | 0.000 | −11.998 | 66.408 | 15.766 | |
| 28 | ∞ | 0.000 | −25.584 | 18.289 | 15.766 | |
| IMG | ∞ | 0.000 | −31.018 | −0.958 | 15.766 | |

Figure 5:
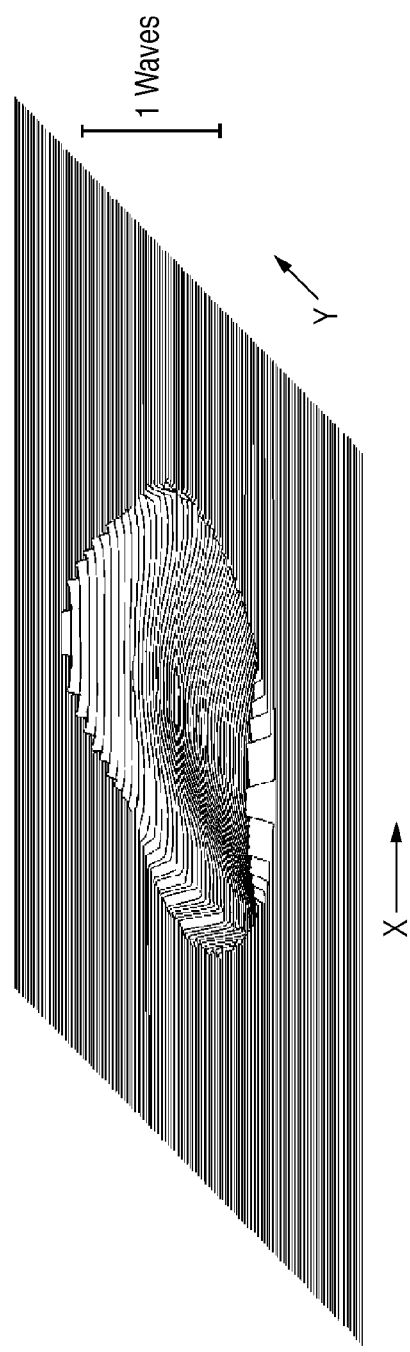
FIG. 5 is a view for explaining the wavefront aberration of the adaptive optical system according to the first embodiment of the present invention.

FIG. 5 shows the wavefront aberration of the adaptive optical system 101 at this time. If the common optical system 10 is constituted by the two separate concave mirrors 32 and 33 as shown in FIG. 4 as in the prior art, in order to satisfy the amount of wavefront aberration in FIG. 5, it is necessary to double the focal length of the spherical lens to about 200 mm. This doubles the area of the optical system.

This embodiment can shorten the focal length and reduce the number of optical elements to be used, and obviates the need to use an optical system having a complicated shape having a plurality of extremes. Therefore, it is not necessary to use any optical system having a complicated arrangement, and it is possible to implement a compact adaptive optical system.

Even the use of a wavefront correction device having a large diameter will require no increase in cost or complicated arrangement, and can implement a very compact adaptive optical system while sufficiently suppressing residual aberration at the optical system and maintaining high efficiency.

Second Embodiment

Figure 6:
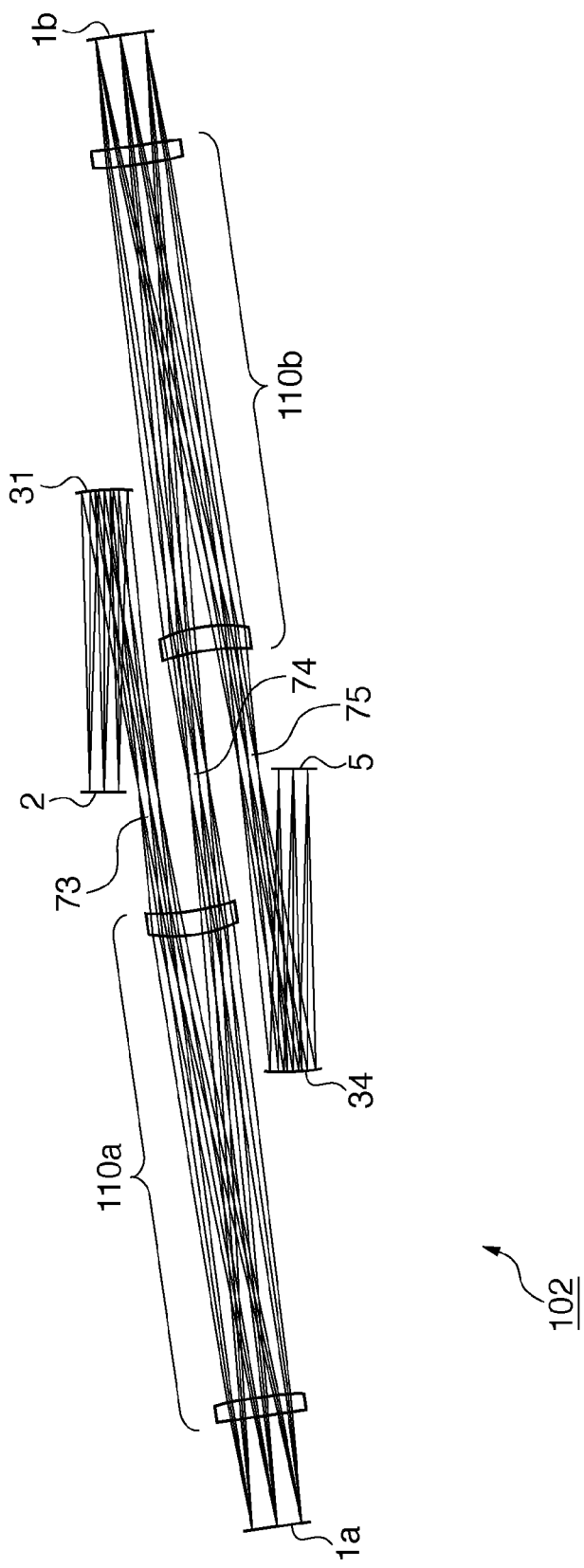
FIG. 6 is a view showing the arrangement of an adaptive optical system according to the second embodiment of the present invention.

The arrangement of an adaptive optical system 102 according to the second embodiment will be described with reference to FIG. 6. The adaptive optical system of this embodiment corrects wavefront aberration by using two deformable mirrors 1a and 1b as two wavefront correction devices. The displacement amount of a deformable mirror of a type having many displacement segments for changing the shape is limited to about several μm in most cases. In contrast, a deformable mirror of a type having a large displacement amount of several tens μm has few segments, and hence cannot reproduce a shape represented by a high-order function. For this reason, it is impossible to correct high-order aberration by using only a deformable mirror of a type having a large displacement amount. The adaptive optical system 102 of this embodiment includes both the different types of deformable mirrors 1a and 1b to correct high-order wavefront aberration by using the former type and correct low-order wavefront aberration by using the latter type. Referring to FIG. 6, two common optical systems 110a (first common optical system) and 110b (second common optical system) each correspond to the common optical system 10 in FIG. 1. The same reference numerals as in FIG. 6 denote the same parts in FIGS. 1 and 2. The common optical system 110a causes light from the first intermediate image irradiated from a light source and condensed to propagate through the first optical path, and makes the propagating light strike the first wavefront correction device 1a. The common optical system 110a then causes the light reflected by the first wavefront correction device 1a to propagate through the second optical path different from the first optical path, and condenses the light as the second intermediate image different from the first intermediate image. The common optical system 110b causes light from the second intermediate image to propagate through the third optical path, and makes the propagating light strike the second wavefront correction device 1b. The common optical system 110b then causes the light reflected by the second wavefront correaction device 1b to propagate through the fourth optical path different from the third optical path, and condenses the light as the third intermediate image different from the second intermediate image.

An optical element 31 (spherical mirror) reflects the beam emitted from a light source (not shown) and collimated by a collimator lens through an optical fiber to form a first intermediate image 73. The common optical system 110a then collimates the beam, which strikes the first wavefront correction device 1a. The beam reflected by the first wavefront correction device 1a is transmitted through the common optical system 110a to form a second intermediate image 74. Thereafter, the beam strikes the common optical system 110b. The beam is collimated by the common optical system 110b again and strikes the second wavefront correaction device 1b. The light reflected by the second wavefront correction device 1b is transmitted through the common optical system 110b again to form a third intermediate image 75. Thereafter, the beam is collimated by an optical element 34 and guided to the deflection element 5 (scanner). At this time, the position corresponding to the wavefront sensor 2, the wavefront correction device 1a, the wavefront correction device 1b, and the deflection element 5 (scanner) have an optically conjugate positional relationship with the eyeball pupil 62 (FIG. 1). The first and second intermediate images 73 and 74 having a conjugate positional relationship with the retina 61 (FIG. 1) are formed on the image plane of the common optical system 110a with the position of the wavefront correction device 1a being a pupil. In addition, the second and third intermediate images 74 and 75 are set on the image plane of the common optical system 110b with the position of the wavefront correction device 1b being a pupil. In this case, the first wavefront correction device 1a is of a type which has many displacement segments and corrects high-order aberration. The second wavefront correction device 1b is of a type which has few segments and corrects low-order aberration. An information processing apparatus 150 obtains wavefront aberration based on the value detected by the wavefront sensor 2, and calculates driving values for the first and second wavefront correction devices 1a and 1b to correct the wavefront aberration. The first and second wavefront correction devices 1a and 1b are driven based on the obtained driving values.

In this embodiment, the first and second wavefront correction devices 1a and 1b have similar diameters, and incident beams on them have the same diameter. Therefore, the common optical systems 110a and 110b each are identical to the common optical system 10 in FIG. 2. If beams having different diameters are to strike the common optical systems 110a and 110b, the focal lengths and pupil diameters of the common optical systems 110a and 110b may be set in accordance with the ratio between the beam diameters.

This embodiment can more accurately correct wavefront aberration by using a plurality of types of wavefront correction devices.

In addition, it is possible to implement a compact adaptive optical system while sufficiently suppressing the residual aberration of the optical system and maintaining efficiency.

Third Embodiment

Figure 7:
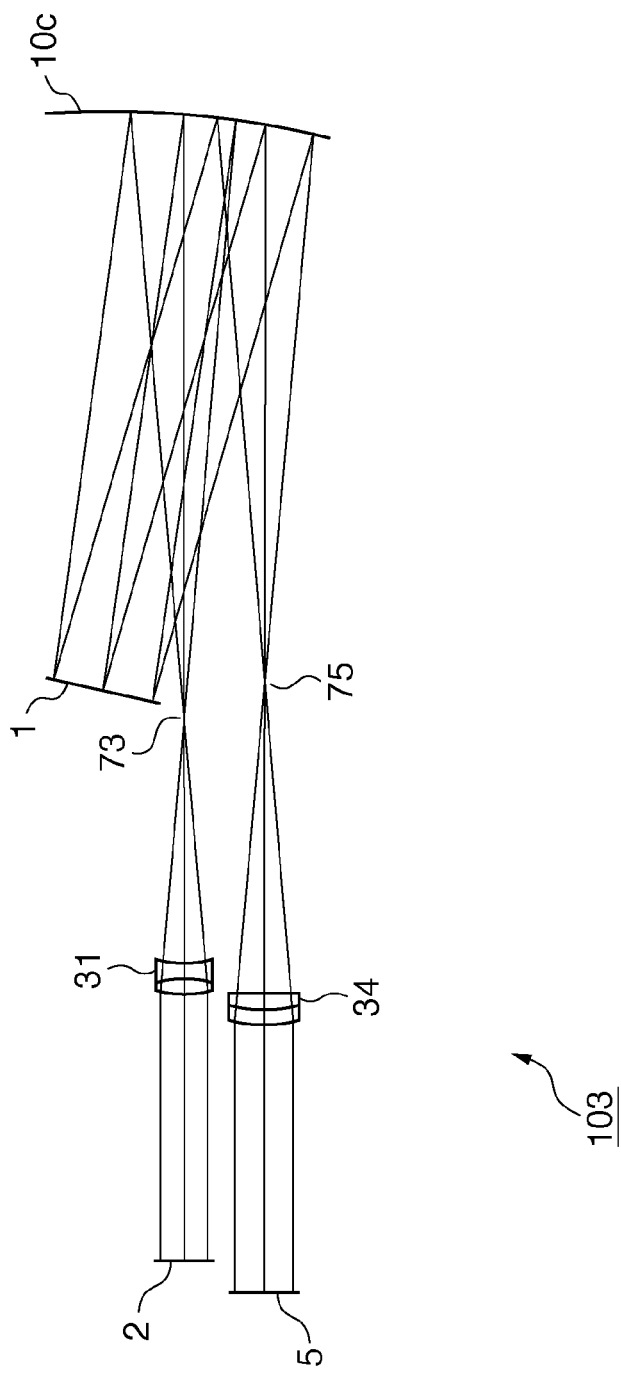
FIG. 7 is a view showing the arrangement of an adaptive optical system according to the third embodiment of the present invention.

The arrangement of an adaptive optical system 103 according to the third embodiment will be described with reference to FIG. 7. This embodiment will exemplify an arrangement using a concave mirror 10c as a common optical system. The same reference numerals as in FIGS. 1 and 2 denote the same parts in FIG. 7, and a description of them will be omitted.

An optical element 31 (lens) forms the beam emitted from a light source (not shown) and collimated by a collimator lens through an optical fiber into a first intermediate image 73. The beam is then collimated by the concave mirror 10c and strikes a wavefront correction device 1. The beam reflected by the wavefront correction device 1 strikes the concave mirror 10c again. The beam reflected by the concave mirror 10c then forms a second intermediate image 74. The beam is collimated by an optical element 34 (lens) and guided to a deflection element 5 (scanner). At this time, a position corresponding to a wavefront sensor 2, the wavefront correction device 1, and the deflection element 5 (scanner) have an optically conjugate positional relationship with the eyeball pupil (62 in FIG. 1). In addition, a first intermediate image 73 and the second intermediate image 74, which have a conjugate positional relationship with the retina (61 in FIG. 1) are set on the image plane of an optical system including the concave mirror 10c with the position of the wavefront correction device 1 being a pupil. As described above, even when the concave mirror 10c is used as a common optical system, since it is not necessary to separate incident beam from reflected beam on the concave mirror 10c, it is possible to reduce the incident angle of light on the wavefront correction device 1 and to set a short focal length for the concave mirror 10c.

This embodiment obviates the need to use any complicated arrangement and can implement a compact adaptive optical system.

Other Embodiments

The adaptive optical systems described in the first to third embodiments can be applied to an image generating apparatus. As an image generating apparatus, for example, an SLO (Scanning Laser Ophthalmoscope) which acquires a two-dimensional image of the retina as a plane is available. In addition, an OCT (Optical Coherence Tomography) which noninvasively acquires a tomogram of the retina can be applied to the image generating apparatus. The image generating apparatus includes any one of the adaptive optical systems described in the first to third embodiments, a detection unit which detects the intensity of return light from an object to be detected, which has undergone aberration correction by the adaptive optical system, and a generation unit which generates an image of the object based on the detection result obtained by the detection unit.

Aspects of the present invention can also be realized by a computer of a system or apparatus (or devices such as a CPU or MPU) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-113423, filed May 17, 2010, which is hereby incorporated by reference herein in its entirety.

What is claimed is:

1. An ophthalmic apparatus comprising:
 an aberration correction unit adapted to correct aberration occurring in light irradiating an eye to be examined; and
 a common optical system commonly provided for an optical path of irradiated light on the aberration correction unit and an optical path of reflected light from the aberration correction unit,
 wherein the common optical system includes at least one optical element, and
 wherein areas through which the irradiated light and the reflected light respectively pass overlap each other on the at least one optical element.

2. The ophthalmic apparatus according to claim 1, wherein the common optical system includes a plurality of optical elements, and
wherein the areas through which the irradiated light and the reflected light respectively pass overlap each other on an optical element, of the plurality of optical elements, which is provided at a position near the aberration correction unit.

3. The ophthalmic apparatus according to claim 1, further comprising:
a first optical element different from the common optical system provided on the optical path of the irradiated light; and
a second optical element different from the common optical system provided on the optical path of the reflected light,
wherein optical axes of the first optical element and second optical element are shifted to an optical axis side of the common optical system.

4. The ophthalmic apparatus according to claim 3, wherein an image plane, including a first intermediate image between the common optical system and the first optical element and a second intermediate image between the common optical system and the second optical element, is curved.

5. The ophthalmic apparatus according to claim 1, further comprising:
an aberration measurement unit adapted to measure aberration occurring in light from the eye,
wherein the aberration measurement unit is placed at a position optically conjugate to an anterior ocular segment of the eye to be examined through the common optical system, and
wherein the aberration correction unit corrects aberration based on a measurement result obtained by the aberration measurement unit.

6. The ophthalmic apparatus according to claim 5, wherein the aberration measurement unit includes a Shack-Hartmann wavefront sensor.

7. The ophthalmic apparatus according to claim 1, wherein the aberration correction unit is placed at a position optically conjugate to an anterior ocular segment of the eye to be examined through the common optical system, and
wherein the aberration correction unit includes at least one of a reflection type deformable mirror and a reflection type spatial optical modulator.

8. The ophthalmic apparatus according to claim 1, further comprising a scanning unit configured to scan a light beam to be irradiated to a fundus of the eye to be examined,
wherein the scanning unit is placed at a position optically conjugate to the aberration correction unit through the common optical system.

9. The ophthalmic apparatus according to claim 1, wherein the at least one optical element includes an optical element of an aspherical shape.

10. The ophthalmic apparatus according to claim 9, wherein the optical element of the aspherical shape has a single extreme.

11. The ophthalmic apparatus according to claim 9, wherein the optical element of the aspherical shape includes an aspherical lens, and
wherein areas through which the irradiated light and the reflected light respectively pass overlap each other on a surface of the aspherical lens.

12. The ophthalmic apparatus according to claim 1, wherein the at least one optical element includes a concave mirror.

13. The ophthalmic apparatus according to claim 1, further comprising:
a detection unit configured to detect reflected light from the eye to be examined, which has undergone aberration correction by the aberration correction unit; and
a generation unit configured to generate a fundus image of the eye to be examined based on a detection result of the detection unit.

14. An adaptive optical system comprising:
a wavefront sensor which receives reflected light of light irradiated from a light source to an object to be detected and detects a wavefront of the object;
a wavefront correction unit placed at a position optically conjugate to the wavefront sensor and adapted to correct wavefront aberration obtained based on a detection result on the wavefront detected by the wavefront sensor; and
a common optical system which causes light from a first intermediate image irradiated from the light source and condensed to propagate through a first optical path, causes the propagating light to strike the wavefront correction unit, causes light reflected by the wavefront correction unit to propagate through a second optical path different from the first optical path, and condenses the light as a second intermediate image different from the first intermediate image,
wherein the common optical system includes at least one optical element, and
wherein the wavefront correction unit is placed at a position of an incident pupil of the common optical system, and the first intermediate and the second intermediate image are condensed on an image plane of the common optical system having the incident pupil.

15. The adaptive optical system according to claim 14, wherein the at least one optical element used for the common optical system includes an aspherical shape having a single extreme.

16. The adaptive optical system according to claim 14, wherein the common optical system comprises a confocal optical system having, as an optical axis, an axis which passes through a reflecting point of a principal ray striking the wavefront correction unit and is perpendicular to the wavefront correction unit.

17. The adaptive optical system according to claim 14, further comprising:
a second wavefront correction unit placed at an optical position relative to the wavefront sensor and the wavefront correction unit and adapted to correct wavefront aberration obtained based on a detection result on the wavefront detected by the wavefront sensor; and
a second common optical system which causes light from a second intermediate image to propagate through a third optical path, causes the propagating light to strike the second wavefront correction unit, causes light reflected by the second wavefront correction unit to propagate through a fourth optical path different from the third optical path, and condenses the light as a third intermediate image different from the second intermediate image,
wherein the second intermediate image and the third intermediate image are condensed on an image plane of the second common optical system.

18. The adaptive optical system according to claim 17, wherein focal lengths are respectively set for the common optical system and the second common optical system based on a ratio between a diameter of light striking the common optical system and a diameter of light striking the second common optical system.

19. An image generating apparatus comprising:
an adaptive optical system defined by claim 14;
a detection unit adapted to detect reflected light from an object to be detected, which has undergone wavefront aberration correction by the adaptive optical system; and
a generation unit adapted to generate an image of the object based on a detection result obtained by the detection unit.

20. The adaptive optical system according to claim 14, wherein an image plane, including the first intermediate image and the second intermediate image, is curved.

21. The adaptive optical system according to claim 14, wherein the least one optical element includes an aspherical lens, and
wherein areas through which the irradiated light and the reflected light respectively pass overlap each other on a surface of the aspherical lens.

22. The adaptive optical system according to claim 14, wherein the at least one optical element includes a concave mirror.

23. The adaptive optical system according to claim 14, wherein areas through which the irradiated light and the reflected light respectively pass overlap each other on the at least one optical element.

24. The adaptive optical system according to claim 23, wherein the common optical system includes a plurality of optical elements, and
wherein the areas through which the irradiated light and the reflected light respectively pass overlap each other on an optical element, of the plurality of optical elements, which is provided at a position near the aberration correction unit.

25. The adaptive optical system according to claim 14, wherein the object to be detected includes an eye to be examined,
wherein the wavefront correction unit is placed at a position optically conjugate to an anterior ocular segment of the eye to be examined through the common optical system, and
wherein the wavefront correction unit includes at least one of a reflection type deformable mirror and a reflection type spatial optical modulator.

26. The adaptive optical system according to claim 25, further comprising a scanning unit configured to scan a light beam to be irradiated to a fundus of the eye to be examined,
wherein the scanning unit is placed at a position optically conjugate to the wavefront correction unit through the common optical system.

27. A control method of an ophthalmic apparatus, the ophthalmic apparatus comprising (a) an aberration correction unit adapted to correct aberration occurring in light irradiating an eye to be examined, and (b) a common optical system commonly provided for an optical path of irradiated light on the aberration correction unit and an optical path of reflected light from the aberration correction unit, wherein the common optical system includes at least one optical element, and wherein areas through which the irradiated light and the reflected light respectively pass overlap each other on the at least one optical element, the method comprising:
a detection step of detecting reflected light from the eye to be examined, which has undergone aberration correction by the aberration correction unit; and
a generation step of generating a fundus image of the eye to be examined based on a detection result of the detection step.

28. A non-transitory computer-readable storage medium storing a computer program which makes a computer execute a control method defined by claim 27.

29. An image generation method using an adaptive optical system, the adaptive optical system comprising (a) a wavefront sensor which receives reflected light of light irradiated from a light source to an object to be detected and detects a wavefront of the object, (b) a wavefront correction unit placed at a position optically conjugate to the wavefront sensor and adapted to correct wavefront aberration obtained based on a detection result on the wavefront detected by the wavefront sensor, and (c) a common optical system which causes light from a first intermediate image irradiated from the light source and condensed to propagate through a first optical path, causes the propagating light to strike the wavefront correction unit, causes light reflected by the wavefront correction unit to propagate through a second optical path different from the first optical path, and condenses the light as a second intermediate image different from the first intermediate image, wherein the common optical system includes at least one optical element, and wherein the wavefront correction unit is placed at a position of an incident pupil of the common optical system, and the first intermediate and the second intermediate image are condensed on an image plane of the common optical system having the incident pupil, the method comprising:
a detection step of detecting reflected light from the object to be detected, which has undergone aberration correction by the adaptive optical system; and
a generation step of generating an image of the object to be detected based on a detection result of the detection step.

30. A non-transitory computer-readable storage medium storing a computer program which makes a computer execute an image generation method defined by claim 29.

* * * * *